(12) United States Patent
Uvnäs-Moberg et al.

(10) Patent No.: US 7,405,200 B2
(45) Date of Patent: Jul. 29, 2008

(54) USE OF OXYTOCIN FOR THE PREPARATION OF A PHARMACEUTICAL COMPOSITION AGAINST CANCER IN SITU AND CERVICITIS

(76) Inventors: Kerstin Uvnäs-Moberg, Sveavagen 9D, Djursholm (SE) S-182 62; Thomas Lundeberg, Hojdstigen 7, Lidingo (SE) S-181 31

( * ) Notice: Subject to any disclaimer, the term of this patent is extended or adjusted under 35 U.S.C. 154(b) by 0 days.

(21) Appl. No.: 10/469,255

(22) PCT Filed: Feb. 28, 2002

(86) PCT No.: PCT/SE02/00362

§ 371 (c)(1),
(2), (4) Date: Apr. 9, 2004

(87) PCT Pub. No.: WO02/067974

PCT Pub. Date: Sep. 6, 2002

(65) Prior Publication Data

US 2004/0176284 A1    Sep. 9, 2004

(30) Foreign Application Priority Data

Feb. 28, 2001   (SE)   .................................. 0100684

(51) Int. Cl.
A61K 38/12 (2006.01)
A61K 38/00 (2006.01)
A61K 38/02 (2006.01)
A61K 38/08 (2006.01)
C07K 2/00 (2006.01)
C07K 7/64 (2006.01)
C07K 5/12 (2006.01)
C07K 7/04 (2006.01)

(52) U.S. Cl. .................. 514/11; 514/2; 514/9; 514/15; 514/16; 530/300; 530/317; 530/328; 530/329

(58) Field of Classification Search ........................ None
See application file for complete search history.

(56) References Cited

U.S. PATENT DOCUMENTS 4,402,942 A    9/1983 Melin 6,262,021 B1 *  7/2001 Uvnas-Moberg et al. ...... 514/11

FOREIGN PATENT DOCUMENTS

| DE | 42 36 293 A1 | 3/1993 |
| DE | 4229878 A1 * | 3/1994 |
| DE | 4244639 A1 * | 7/1994 |
| WO | WO9843660 A1 * | 10/1998 |
| WO | WO9843661 A1 * | 10/1998 |
| WO | 00/18424 | 4/2000 |
| WO | WO 200018424 A1 * | 4/2000 |
| WO | 01/78758 A1 | 10/2001 |
| WO | WO 03017922 A2 * | 6/2003 |

OTHER PUBLICATIONS

D. Kornfeld, et al. Gut. (1997) 41, pp. 522-525.*
J.A. Eaden, et al. Gut. (2001) 48, 526-535.*
A. Ekbom, et al. N. Engl. J. Med. (1990) 323(18), pp. 1228-1233.*
B. Jancin. "Data from two studies: fibromyalgia patients may have higher Ca risk." OB/GYN News Sep. 15, 2004, 2 pages.*
K.B. Michels, et al. Diabetes Care (2003) 26(6), pp. 1752-1758.*
R. Talamini, et al. Brit. J. Cancer. (1997) 75(11), pp. 1699-1703.*
M.E. DelGiudice, et al. Breast Cancer Res. Treat. (1998) 47, pp. 111-120.*
Gianni Bussolai et al., "In-labeled 1,4,7,10-Tetraazacyclododecane-$N,N',N'',N'''$-tetraacetic Acid-Lys$^8$-Vasotocin: A New Powerful Radioligand for Oxytocin Receptor-expressing Tumors," Cancer Research, V. 61, 2001, pp. 4393-4397.
Paola Cassoni et al., "Oxytocin Receptors in Human Adenocarcinomas of the Endomtrium: Presence and Biological Signifcance," Journal of Pathology, V. 190, 2000, pp. 470-477.
STN International, File CA, Chemical abstracts, accession No. 111:233675, Petr Simek et al., "Preparation of [2-(0-methyltrosine)] deamino-1-carbaoxytocin by a combined solid phase and solution method," 1998, two pages.
STN International, File CAPLUS, CAPLUS accession No. 1969:47836, document No. 70:47836, Haruhiko Aoyagi et al., "Analogs of oxytocin containing leucinamide and glycylcinamide in place of glycinamide," & Bull. Chem. Soc. Jap., 1968, V. 41, pp. 2772-2776.
STN International, File CA, Chemical abstracts, accession No. 90:6683, Roger Freidinger et al., "Titanium (III) as a selective reducing agent for nitroarginyl peptides: synthesis of arginine vasotocin," & J. Org. Chem., 1978, V. 43, pp. 4800-4803.

* cited by examiner

*Primary Examiner*—Cecilia J. Tsang
*Assistant Examiner*—Andrew D. Kosar
(74) *Attorney, Agent, or Firm*—Young & Thomson

(57) ABSTRACT

A method of treating cancer in situ and cervicitis is disclosed. A pharmaceutical composition comprising at least one substance with oxytocin activity against cancer in situ and cervicitis and compound of the formula SEQ ID NO:2 is also disclosed.

11 Claims, No Drawings

SEQUENCE LISTING

```
<160> NUMBER OF SEQ ID NOS: 24

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 1
```

```
Cys Tyr Ile Gln Asn Cys Pro Leu Gly
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys or not present
<220> FEATURE:
<221> NAME/KEY: MOD_RES
<222> LOCATION: (2)
<223> OTHER INFORMATION: Tyr, (O-methyl-Tyr), Phe or not present
<220> FEATURE:
<221> NAME/KEY: MOD_RES
<222> LOCATION: (3)
<223> OTHER INFORMATION: Ile, Val, Hoph, Phe, Cha or not present
<220> FEATURE:
<221> NAME/KEY: MOD_RES
<222> LOCATION: (4)
<223> OTHER INFORMATION: Gln, Ser, Thr, Cit, Arg or not present
<220> FEATURE:
<221> NAME/KEY: MOD_RES
<222> LOCATION: (7)
<223> OTHER INFORMATION: Pro or not present
<220> FEATURE:
<221> NAME/KEY: MOD_RES
<222> LOCATION: (8)
<223> OTHER INFORMATION: Ile, Leu, Val, Hos, Thr, Arg, Cit or not
      present
<220> FEATURE:
<221> NAME/KEY: MOD_RES
<222> LOCATION: (9)
<223> OTHER INFORMATION: Gly, Ala or not present
<220> FEATURE:
<221> NAME/KEY: MOD_RES
<222> LOCATION: (10)
<223> OTHER INFORMATION: Gly or not present
<220> FEATURE:
<223> OTHER INFORMATION: This peptide may encompass 2-10 residues and is
      c-term amidated; see specification for preferred embodiments.
<220> FEATURE:
<223> OTHER INFORMATION: c-term amidated

<400> SEQUENCE: 2

Xaa Xaa Xaa Xaa Asn Cys Xaa Xaa Xaa Xaa
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 3

Cys Tyr Ile Gln Asn Cys Pro Ile Gly
 1               5

<210> SEQ ID NO 4
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 4

Cys Tyr Ile Ser Asn Cys Pro Ile Gly
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 5

Cys Phe Val Arg Asn Cys Pro Thr Gly
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 6

Cys Tyr Ile Gln Asn Cys Pro Arg Gly
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 7

Cys Tyr Phe Gln Asn Cys Pro Arg Gly
  1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 8

Cys Tyr Ile Gln Asn Cys Pro Leu Gly Gly
 1               5                  10

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 9

Cys Tyr Ile Gln Asn Cys
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 10

Cys Tyr Ile Gln Asn Cys Pro
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 11

Cys Tyr Ile Gln Asn Cys Pro Leu
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated
```

<400> SEQUENCE: 12

Tyr Ile Gln Asn Cys Pro Leu Gly
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 13

Ile Gln Asn Cys Pro Leu Gly
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 14

Gln Asn Cys Pro Leu Gly
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 15

Ile Gln Asn Cys Pro
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Cha
<220> FEATURE:
<221> NAME/KEY: MOD_RES
<222> LOCATION: (4)
<223> OTHER INFORMATION: Cit
<220> FEATURE:
<221> NAME/KEY: DISULFID
<222> LOCATION: (1)..(6)
<220> FEATURE:
<223> OTHER INFORMATION: c-term amidated

<400> SEQUENCE: 16

Cys Tyr Xaa Xaa Asn Cys Pro Arg Gly

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 17

Cys Tyr Val Thr Asn Cys Pro Leu Gly
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hoph
<220> FEATURE:
<221> NAME/KEY: DISULFID
<222> LOCATION: (1)..(6)
<220> FEATURE:
<223> OTHER INFORMATION: c-term amidated

<400> SEQUENCE: 18

Cys Tyr Xaa Thr Asn Cys Pro Val Gly
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Cit
<220> FEATURE:
<221> NAME/KEY: DISULFID
<222> LOCATION: (1)..(6)
<220> FEATURE:
<223> OTHER INFORMATION: c-term amidated

<400> SEQUENCE: 19

Cys Tyr Phe Xaa Asn Cys Pro Leu Gly
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Cha

```
<220> FEATURE:
<221> NAME/KEY: MOD_RES
<222> LOCATION: (8)
<223> OTHER INFORMATION: Hos
<220> FEATURE:
<221> NAME/KEY: DISULFID
<222> LOCATION: (1)..(6)
<220> FEATURE:
<223> OTHER INFORMATION: c-term amidated

<400> SEQUENCE: 20

Cys Tyr Xaa Arg Asn Cys Pro Xaa Ala
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(5)
<220> FEATURE:
<223> OTHER INFORMATION: c-term amidated

<400> SEQUENCE: 21

Cys Tyr Val Asn Cys Pro Ala
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hoph
<220> FEATURE:
<221> NAME/KEY: MOD_RES
<222> LOCATION: (7)
<223> OTHER INFORMATION: Cit
<220> FEATURE:
<221> NAME/KEY: DISULFID
<222> LOCATION: (1)..(5)
<220> FEATURE:
<223> OTHER INFORMATION: c-term amidated

<400> SEQUENCE: 22

Cys Tyr Xaa Asn Cys Pro Xaa Ala
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)
<220> FEATURE:
<223> OTHER INFORMATION: c-term amidated

<400> SEQUENCE: 23

Cys Tyr Phe Arg Asn Cys Pro Val Ala
 1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: (O-methyl-Tyr)
<220> FEATURE:
<223> OTHER INFORMATION: c-term amidated

<400> SEQUENCE: 24

Xaa Ile Gln Asn Cys Pro Leu Gly
 1               5
```

USE OF OXYTOCIN FOR THE PREPARATION OF A PHARMACEUTICAL COMPOSITION AGAINST CANCER IN SITU AND CERVICITIS

The present invention relates to the use of substances with oxytocin activity for the preparation of a pharmaceutical composition against cancer in situ and cervicitis. It also relates to a pharmaceutical composition comprising at least one substance with oxytocin activity against cancer in situ and cervicitis. It also relates to a compound of the formula SEQ ID NO: 2.

BACKGROUND OF THE INVENTION

Oxytocin was one of the first peptide hormones to be isolated and sequenced. It is a nonapeptide with two cysteine residues that form a disulfide bridge between positions 1 and 6 and corresponds to the formula

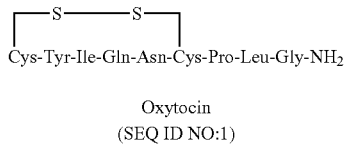

Oxytocin
(SEQ ID NO:1)

For a long time the only effects attributed to oxytocin were its stimulating effects on milk ejection and uterine contractions, but in the past decades it has been shown that oxytocin exerts a wide spectrum of effects within the central nervous system, CNS. It has been suggested that oxytocin participates in the control of memory and learning processes and of various types of behaviour such as feeding, locomotion, as well as maternal and sexual behaviour. Oxytocin is also suggested to participate in the control of cardiovascular functions, thermoregulation, and pain threshold and fluid balance. There is also evidence that oxytocin is involved in the control of various immunological processes. It has recently been demonstrated that oxytocin injections cause a lowering of blood pressure and increased weight gain—long lasting effects after repetitive administration. As a central stimulating substance oxytocin plays an important role in the interaction between mother and progeny in mammals. The products may also be used prophylactic in young human beings e.g. already in new born babies or young children to prevent the development of diseases later on in life which diseases are dependent on stress conditions during the fetal life. Such conditions may be heart/vessel diseases such as stroke, heart infarct, hypertension, and diabetes.

In the human body oxytocin is produced in the paraventricular nucleus, PVN, and the supraoptic nucleus, SON, of the hypothalamus. It differs by only two amino acids from vasopressin, which is also produced in these nuclei. The magnocellular oxytocinergic neurones of the SON and PVN send oxons to the posterior pituitary from which oxytocin is released into the circulation. Parvocellular neurones that originate in the PVN project into multiple areas within CNS. The oxytocin-producing cells are innervated by cholinergic, catecholaminergic as well as peptidergic neurones. The presence of oxytocin in different tissues outside the brain, such as the uterus, ovaries, testis, thymus, adrenal medulla and pancreas has been demonstrated and oxytocin is suggested to exert local effects in these organs.

A parallel secretion of oxytocin into the brain regions and into the circulation occurs in response to some stimuli such as suckling, but other stimuli can cause separate activation of oxytocinergic neurones, terminating in the brain or the pituitary.

It has now turned out that oxytocin has a relieving effect on cancer in situ and cervicitis.

There are several oxytocin derivatives, i.e. compounds with a structure similar to that of oxytocin. There are preliminary indications that other oxytocin derivatives than oxytocin could give the effects against cancer in situ and cervicitis as well as parts of the oxytocin molecule. No publications describe the use of oxytocin or any other oxytocin derivatives or parts of the oxytocin molecule to have effects against cancer in situ and cervicitis.

By the expression "cancer in situ and cervicitis" we understand consequences of diseases in vagina and cervix originating from infections, as well as inflammations. In the context of the invention, cancer in situ is related to the cervix. Such diseases include, besides cancer in situ and cervicitis, also precancerous disease states, squamous cell carcinoma, and koilocytosis. By cancer in situ is meant a neoplastic entity wherein the tumour cells are confined to the epithelium of origin, without invasion of the basement membrane. By cervicitis is meant inflammation of the cervix uteri i e the lower and narrow end of the uterus, between the isthmus and the ostium uteri. The epithelium of the cervix uteri is quite different from the epithelium of the rest of the uterus. Koilocytosis is a consequence of herpes virus.

Bussolati et al., Cancer Research, Volume 61, June 2001, p. 4393-4397, describes that oxytocin derivatives may have effects against OTR-positive tumours, such as breast and endometrial carcinomas, neuroblastomas, and glioblastomas. Furthermore, Cassoni et al., Journal of Pathology, Volume 190, 2000, p. 470-477, describes that oxytocin reduces cell proliferation in breast cancer cells, in neural neoplastic cells, as well as in a human endometrial carcinoma cell line. However, these documents relate to the treatment of advanced cancer forms, whereas the present invention relates to the treatment of cancer at a very early stage, e g precancerous disease states as mentioned above. The effects of oxytocin derivatives against such an early cancer are most probably due to antioxidant effects of oxytocin or metabolites thereof such as cysteine and N-acetylcysteine. In van Zandwijk et al., J Cell Biochem Suppl 1995, Vol. 22, p. 24-32, it is stated that the antimutagenic and anticarcinogenic effects of N-acetylcysteine could be ascribed to e g the antioxidant activity thereof.

It has now turned out that oxytocin improves recovery of cancer in situ and cervicitis (Example 1). This example indicates that oxytocin or that substances with oxytocin activity may be used against cancer in situ and cervicitis. However, it should be noted that it is not necessary that the patients treated according to Example 1 have postmenopausal disorders before treatment.

The effect of oxytocin can be extended or strengthened by administration in combination with drugs increasing the release of oxytocin and/or the number or the affinity of oxytocin receptors. One such drug is oestrogen. The effect of oxytocin can also be extended or strengthened by administration in combination with drugs having an $\alpha_2$-agonistic effect. One such drug is clonidine.

SUMMARY OF THE INVENTION

The present invention relates to the use of at least one substance with oxytocin activity for the preparation of a pharmaceutical composition against cancer in situ and cervicitis. The invention also relates to a pharmaceutical composition comprising an effective concentration of at least one substance with oxytocin activity in mixture or otherwise together with at least one pharmaceutically acceptable carrier or excipient. Such a pharmaceutical composition could be used in order to achieve a relieving effect on cancer in situ and cervicitis.

DETAILED DESCRIPTION OF THE INVENTION

One object of the present invention is the use of at least one substance with oxytocin activity for the preparation of a pharmaceutical composition against cancer in situ and cervicitis.

It is preferred that the at least one substance is selected from the group consisting of the following compounds:

(SEQ ID NO: 2)

$X_1$-$X_2$-$X_3$-$X_4$-Asn-Cys-$X_5$-$X_6$-$X_7$-$X_8$-$NH_2$ wherein $X_1$ is selected firm the group consisting of Cys, Mpa and nothing, $X_2$ is selected from the group consisting of Tyr, (O-methyl-Tyr), Phe, and nothing, $X_3$ is selected from the group consisting of Ile, Val, Hoph, Phe, Cha, and nothing, $X_4$ is selected from the group consisting of Gln, Ser, Thr, Cit, Arg, and Daba, $X_5$ is selected from the group consisting of Pro, and nothing, $X_6$ is selected from the group consisting of Ile, Leu, nothing, Val, Hos, Daba, Thr, Arg, and Cit, $X_7$ is selected from the group consisting of Gly, nothing, and Ala, $X_8$ is selected from the group consisting of Gly, and nothing, $X_9$ is selected from the group consisting of $CH_2$ and S;

as well as salts thereof.

The cystein disulfide bridge is only present when $X_1$ represents Cys or Mpa, $X_2$ represents Tyr, (O-methyl-Tyr) or Phe, and $X_3$ represents Ile, Val, Hoph, Phe or Cha.

By "nothing" is meant that the letters respectively may have no meaning or may represent a bond and that there may be a direct bond between the items (letter, atom or group) situated to the right and to the left, respectively, of the letter designating "nothing". For example, in SEQ ID NO: 2 above, when only $X_1$ designates nothing, the resulting molecule corresponds to $X_2$-$X_3$-$X_4$-Asn-Cys-$X_5$-$X_6$-$X_7$-$X_8$-$NH_2$. When only $X_8$ designates nothing, the $X_7$ residue is amidated.

It is even more preferred that the at least one substance is selected from the group consisting of the following compounds:

Cys-Tyr-Ile-Gln-Asn-Cys-Pro-Leu-Gly-$NH_2$

Oxytocin
(SEQ ID NO:1)

$X_1$ is Cys, $X_2$ is Tyr, $X_3$ is Ile, $X_4$ is Gln, $X_5$ is Pro, $X_6$ is Leu, $X_7$ is Gly, $X_8$ is nothing, and $X_9$ is S in Claim 2 and 7

Cys-Tyr-Ile-Gln-Asn-Cys-Pro-Ile-Gly-$NH_2$

Mesotocin
(SEQ ID NO:3)

$X_1$ is Cys, $X_2$ is Tyr, $X_3$ is Ile, $X_4$ is Gln, $X_5$ is Pro, $X_6$ is Ile, $X_7$ is Gly, $X_8$ is nothing, and $X_9$ is S in Claim 2 and 7

Cys-Tyr-Ile-Ser-Asn-Cys-Pro-Ile-Gly-$NH_2$

Isotocin
(SEQ ID NO:4)

$X_1$ is Cys, $X_2$ is Tyr, $X_3$ is Ile, $X_4$ is Ser, $X_5$ is Pro, $X_6$ is Ile, $X_7$ is Gly, $X_8$ is nothing, and $X_9$ is S is Claim 2 and 7

Cys-Phe-Val-Arg-Asn-Cys-Pro-Thr-Gly-$NH_2$

Annetocin
(SEQ ID NO:5)

$X_1$ is Cys, $X_2$ is Phe, $X_3$ is Val, $X_4$ is Arg, $X_5$ is Pro, $X_6$ is Thr, $X_7$ is Gly, $X_8$ is nothing, and $X_9$ is S in Claim 2 and 7

(SEQ ID NO: 6)

Cys-Tyr-Ile-Gln-Asn-Cys-Pro-Arg-Gly-$NH_2$

Vasotocin $X_1$ is Cys, $X_2$ is Tyr, $X_3$ is Ile, $X_4$ is Gln, $X_5$ is Pro, $X_6$ is Arg, $X_7$ is Gly, $X_8$ is nothing, and $X_9$ is S in Claim 2 and 7

(SEQ ID NO: 7)

Cys-Tyr-Phe-Gln-Asn-Cys-Pro-Arg-Gly-$NH_2$

Vasopressin $X_1$ is Cys, $X_2$ is Tyr, $X_3$ is Phe, $X_4$ is Gln, $X_5$ is Pro, $X_6$ is Arg, $X_7$ is Gly, $X_8$ is nothing, and $X_9$ is S in Claim 2 and 7

(SEQ ID NO: 8)

Cys-Tyr-Ile-Gln-Asn-Cys-Pro-Leu-Gly-Gly-$NH_2$ $X_1$ is Cys, $X_2$ is Tyr, $X_3$ is Ile, $X_4$ is Gln, $X_5$ is Pro, $X_6$ is Leu, $X_7$ is Gly, $X_8$ is Gly, and $X_9$ is S in Claim 2 and 7

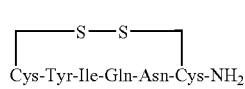

SEQ ID NO: 9

$X_1$ is Cys, $X_2$ is Tyr, $X_3$ is Ile, $X_4$ is Gln, $X_5$–$X_8$ is nothing, and $X_9$ is S in claim 2, 7, and 11

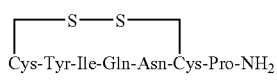

SEQ ID NO: 10

$X_1$ is Cys, $X_2$ is Tyr, $X_3$ is Ile, $X_4$ is Gln, $X_5$ is Pro, $X_6$–$X_8$ is nothing, and $X_9$ is S in Claim 2 and 7

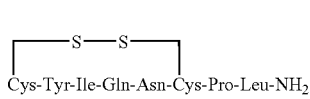

SEQ ID NO: 11

$X_1$ is Cys, $X_2$ is Tyr, $X_3$ is Ile, $X_4$ is Gln, $X_5$ is Pro, $X_6$ is Leu, $X_7$–$X_8$ is nothing, and $X_9$ is S in Claim 2 and 7

```
Tyr-Ile-Gln-Asn-Cys-Pro-Leu-Gly-NH2    SEQ ID NO: 12
```

$X_1$ is nothing, $X_2$ is Tyr, $X_3$ is Ile, $X_4$ is Gln, $X_5$ is Pro, $X_6$ is Leu, $X_7$ is Gly, $X_8$ is nothing, and $X_9$ is S in Claim 2, 7, and 11

```
Ile-Gln-Asn-Cys-Pro-Leu-Gly-NH2    SEQ ID NO: 13
```

$X_1$–$X_2$ is nothing, $X_3$ is Ile, $X_4$ is Gln, $X_5$ is Pro, $X_6$ is Leu, $X_7$ is Gly, $X_8$ is nothing, and $X_9$ is S in Claim 2, 7, and 11

```
Gln-Asn-Cys-Pro-Leu-Gly-NH2    SEQ ID NO: 14
```

$X_1$–$X_3$ is nothing, $X_4$ is Gln, $X_5$ is Pro, $X_6$ is Leu, $X_7$ is Gly, $X_8$ is nothing, and $X_9$ is in Claim 2, 7, and 11

```
Ile-Gln-Asn-Cys-Pro-NH2    SEQ ID NO: 15
```

$X_1$–$X_2$ is nothing, $X_3$ is Ile, $X_4$ is Gln, $X_5$ is Pro, $X_6$–$X_8$ is nothing, and $X_9$ is S in Claim 2, 7, and 11

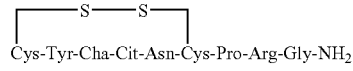

SEQ ID NO: 16

$X_1$ is Cys, $X_2$ is Tyr, $X_3$ is Cha, $X_4$ is Cit, $X_5$ is Pro, $X_6$ is Arg, $X_7$ is Gly, $X_8$ is nothing, and $X_9$ is S in Claim 2 and 7

SEQ ID NO: 17

$X_1$ is Cys, $X_2$ is Tyr, $X_3$ is Val, $X_4$ is Thr, $X_5$ is Pro, $X_6$ is Leu, $X_7$ is Gly, $X_8$ is nothing, and $X_9$ is S in Claim 2 and 7

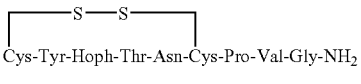

$X_1$ is Cys, $X_2$ is Tyr, $X_3$ is Hoph, $X_4$ is Thr, $X_5$ is Pro, $X_6$ is Val, $X_7$ is Gly, $X_8$ is nothing, and $X_9$ is S in Claim 2 and 7

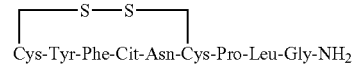

SEQ ID NO: 19

$X_1$ is Cys, $X_2$ is Tyr, $X_3$ is Phe, $X_4$ is Cit, $X_5$ is Pro, $X_6$ is Leu, $X_7$ is Gly, $X_8$ is nothing, and $X_9$ is S in Claim 2 and 7

SEQ ID NO: 20

$X_1$ is Cys, $X_2$ is Tyr, $X_3$ is Cha, $X_4$ is Arg, $X_5$ is Pro, $X_6$ is Hos, $X_7$ is Ala, $X_8$ is nothing, and $X_9$ is S in Claim 2 and 7

SEQ ID NO: 21

Cys-Tyr-Val-Daba-Asn-Cys-Pro-Daba-Ala-NH2

$X_1$ is Cys, $X_2$ is Tyr, $X_3$ is Val, $X_4$ is Daba, $X_5$ is Pro, $X_6$ is Daba, $X_7$ is Ala, $X_8$ is nothing, and $X_9$ is S in Claim 2 and 7

SEQ ID NO: 22

Cys-Tyr-Hoph-Daba-Asn-Cys-Pro-Cit-Ala-NH2

$X_1$ is Cys, $X_2$ is Tyr, $X_3$ is Hoph, $X_4$ is Daba, $X_5$ is Pro, $X_6$ is Cit, $X_7$ is Ala, $X_8$ is nothing, and $X_9$ is S in Claim 2 and 7

Cys-Tyr-Phe-Arg-Asn-Cys-Pro-Val-Ala-NH2

SEQ ID NO:23

$X_1$ is Cys, $X_2$ is Tyr, $X_3$ is Phe, $X_4$ is Arg, $X_5$ is Pro, $X_6$ is Val, $X_7$ is Ala, $X_8$ is nothing, and $X_9$ is S in Claim 2 and 7

Mpa-(O—methyl-Tyr)-Ile-Gln-Asn-Cys-Pro-Leu-Gly-NH2

Carbetocin
(SEQ ID NO:24)

$X_1$ is Mpa, $X_2$ is (O-methyl-Tyr), $X_3$ is Ile, $X_4$ is Gln, $X_5$ is Pro, $X_6$ is Leu, $X_7$ is Gly, $X_8$ is nothing, and $X_9$ is $CH_2$ in Claim 2 and 7, wherein Mpa stands for β-mercaptopropionic acid; wherein the CH$_2$—S-group thereof is bonded to the cystein portion via a thioether bond i position 6 giving the structure for SEQ ID NO: 24 as follows:

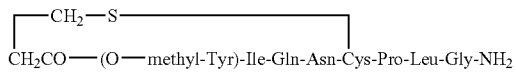

wherein (O-methyl-Tyr) stands for O-methyltyrosine of the chemical formula:

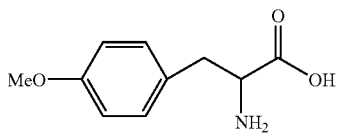

wherein Cha stands for cyclohexylalanine,

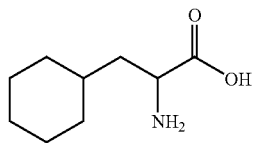

Hoph stands for homophenylalanine,

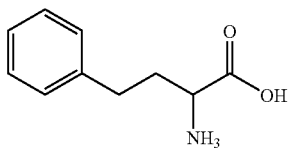

Cit stands for citrulline,

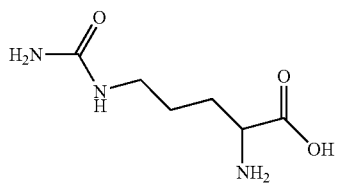

Daba stands for diaminobutyric acid, and

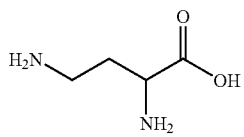

Hos stands for homoserine.

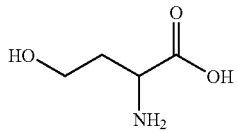

There are different processes described for the synthetical production of oxytocin; commercial processes are for instance described in U.S. Pat. Nos. 2,938,891 and 3,076,797.

A substance with oxytocin activity refers, whenever applicable, in addition to oxytocin also to precursors, metabolic derivatives, oxytocin agonists or analogues displaying the same properties.

Annetocin has been isolated from the earthworm, as described in Oumi T, Ukena K, Matsushima O, Ikeda T, Fujita T, Minakata H, Nomoto K, Annetocin: an oxytocin-related peptide isolated from the earthworm, Eisenia foetida, *Biochem Biophys Res Commun* 1994, Jan. 14, 198(1): 393–399. The uterotonic activity and myometrial receptor affinity of carbetocin is described in Atke A and Vilhardt H, Acta Endocrinologica (Copenh) 1987, 115: 155–160.

Other substances with oxytocin activity could also be used, such as naturally occurring or artificially modified variants, analogues, and derivatives of oxytocin, mesotocin, isotocin, and annetocin. Such substances could be obtained by addition, insertion, elimination, or substitution of at least one amino acid in these hormones. By a substance with an oxytocin like activity is also understood precursors, metabolites such as metabolic derivatives e.g. metabolic degradation products, agonists, or analogues of the substances mentioned herein displaying the same properties. When one or more amino acids are added to a substance with oxytocin activity, it is preferred to add 1–3 amino acids to the carboxyl terminal. Metabolic derivatives or metabolic degradation products may be oxytocin like peptides e.g. with nine amino acids such as oxytocin, mesotocin, isotocin, and annetocin from which one or more amino acids has been deleted from either the carboxyl terminal end or the amino terminal end or both the carboxyl terminal and the amino terminal end, preferably 1–3 amino acids from each terminal. It could be ascertained that these variants are analogues of oxytocin, mesotocin, isotocin or annetocin by immunological methods, e.g. RIA (radioimmunoassay), IRMA (radiometic methods), RIST (radioimmunosorbent test), and RAST (radioallergosorbent test). The invention also includes substances having at least 50, 60, 70, 80 and most preferably 90% homology to oxytocin, and showing oxytocin activity.

As mentioned above, there are indications that addition of one or more amino acids to the oxytocin molecule may give a molecule that has effects against inflammation. One example of such a molecule is SEQ ID NO: 8.

As mentioned above, there are indications that subfragments of the oxytocin molecule have effects against inflammation. Examples of subfragments of the oxytocin molecule are the following compounds: SEQ ID NO: 9, SEQ ID NO: 10, SEQ ID NO: 11, SEQ ID NO: 12, SEQ ID NO: 13, SEQ ID NO: 14, and SEQ ID NO: 15.

There is also a possibility to create new compounds with oxytocin activity by means of computer simulation. Methods for computer simulation are known by a person skilled in the art, e.g. as described in EP 0660 210 A2. Eight new compounds have been created by means of computer simulation, namely the following peptides: SEQ ID NO: 16, SEQ ID NO:

17, SEQ ID NO: 18, SEQ ID NO: 19, SEQ ID NO: 20, SEQ ID NO: 21, SEQ ID NO: 22, and SEQ ID NO: 23.

The invention also relates to the peptides mentioned above in both D- and L-form. Especially the invention relates to the L-form. By inversion of the peptide sequence thereof, the D-form could be converted to the L-form. The effect of the D- and L-forms are the same. These and the peptides above can be produced by methods known to a person skilled in the art, e.g. according to Merrifield, P. B., "Solid Phase Synthesis", *Angew. Chemie*, 1985, No. 97, p. 801.

It is preferred that a substance with oxytocin activity is administered in an amount of 0.01–100 ng/kg body weight of the patient, in particular 0.1–10 ng/kg.

Another object of the invention is a pharmaceutical composition against cancer in situ and cervicitis comprising an effective concentration of at least one substance with oxytocin activity in mixture or otherwise together with at leat least one substance is selected from the group consisting of compounds with the formula SEQ ID NO: 2. It is even more preferred that the at least one substance is selected from the group consisting of the following compounds: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

The pharmaceutical compositions according to the invention may contain substances that extend or strengthen the effects of oxytocin. Such substances could increase the release of oxytocin and/or the number or affinity of oxytocin receptors, such as oestrogen, or drugs having an $\alpha_2$-agonistic effect, such as clonidine.

It should be noted that salts of the compounds according to the invention are included within the scope of the invention. As examples of salts of the compounds are intended in particular pharmaceutically acceptable acid and base addition salts.

The expression "pharmaceutically acceptable acid addition salts" are intended to be any non-toxic organic or inorganic acid addition salt of the compounds of SEQ ID NO: 2. Examples of illustrative inorganic acids that form suitable salts are hydrochloric acid, hydrobromic acid, sulphuric acid, phosphoric acid and acid metal salts such as sodium monohydrogen ortophosphate and potassium hydrogensulphate. Examples of illustrative organic acids that form suitable salts are mono-, di- and tricarboxylic acids. Examples of such acids are acetic acid, glycolic acid, lactic acid, pyruvic acid, malonic acid, succinic acid, glutaric acid, fumaric acid, malic acid, tartaric acid, citric acid, ascorbic acid, maleic acid, hydroxymaleic acid, benzoic acid, hydroxybenzoic acid, phenylacetic acid, cinnamic acid, salicylic acid, 2-phenoxybenzoic acid, and sulphonic acids such as p-toluenesulphonic acid, methanesulphonic acid and 2-hydroxyethanesulphonic acid. Such salts could either be in hydrated or anhydrous form. The acid addition salts of these compounds are generally water soluble and different hydrophilic organic solvents and, that compared to the free base forms thereof, generally display higher melting points.

The expression "pharmaceutically acceptable base addition salts" are intended to be any non-toxic organic or inorganic base addition salt of the compounds of SEQ ID NO: 2. Examples of illustrative inorganic bases that form suitable salts are alkali and earth alkali metal hydroxides and carbonates such as sodium hydroxide, sodium carbonate, potassium hydroxide, potassium carbonate, calcium hydroxide, calcium carbonate, magnesium hydroxide, magnesium carbonate and ammonia. Examples of illustrative organic bases that form suitable salts are methylamine, dimethylamine, trimethylamine and picoline. Either mono- or dibasic salts could be formed with such compounds. The base addition salts of these compounds are generally water soluble and different hydrophilic organic solvents and, that compared to the free base forms thereof, generally display higher melting points.

The pharmaceutical compositions are prepared in a manner known to a person skilled in the pharmaceutical art. The carrier or the excipient could be a solid, semi-solid or liquid material that could serve as a vehicle or medium for the active ingredient. Suitable carriers or excipients are known in the art. The pharmaceutical composition could be adapted to oral, parenteral, intravaginal, or topical use and could be administered to the patient as tablets, capsules, suppositories, solutions, suspensions or the like.

The pharmaceutical compositions could be administered orally, e.g. with an inert diluent or with an edible carrier. They could be enclosed in gelatine capsules or be compressed to tablets. For oral therapeutic administration the compounds according to the invention could be incorporated with excipients and used as tablets, lozenges, capsules, elixirs, suspensions, syrups, wafers, chewing gums and the like. These preparations should contain at least 4% by weight of the compounds according to the invention, the active ingredient, but could be varied according to the special form and could, suitably, be 4–70% by weight of the unit. The amount of the active ingredient that is contained in compositions is so high that a unit dosage form suitable for administration is obtained.

The tablets, pills, capsules, lozenges and the like could also contain at least one of the following adjuvants: binders such as microcrystalline cellulose, gum tragacanth or gelatine, excipients such as starch or lactose, disintegrating agents such as alginic acid, Primogel, corn starch, and the like, lubricants such as magnesium stearate or Sterotex, glidants such as colloidal silica dioxide, and sweetening agents such as saccharose or saccharin could be added or flavourings such as peppermint, methyl salicylate or orange flavouring. When the unit dosage form is a capsule it could contain in addition to the type above a liquid carrier such as polyethylene glycol or a fatty oil. Other unit dosage forms could contain other different materials that modify the physical form of the unit dosage form, e.g. as coatings. Accordingly, tablets or pills could be coated with sugar, shellac or other enteric coating agents. A syrup could in addition to the active ingredient contain saccharose as a sweetening agent and some preservatives, dyes and flavouring agents. Materials that are used for preparation of these different compositions should be pharmaceutically pure and non-toxic in the amounts used.

For parenteral administration the compounds according to the invention could be incorporated in a solution or suspension. Parenteral administration refers to the administration not through the alimentary canal but rather by injection through some other route, as subcutaneous, intramuscular, intraorbital, intracapsular, intraspinal, intrasternal, intravenous, intranasal, intrapulmonary, through the urinary tract, through eye drops, rectal or intravaginal (e.g. as a suppository, a vagitorium, a cream or an ointment), through the lactiferous tract in cattle, into an organ such as bone marrow, etc. Bone marrow may also be treated in vitro. These preparations could contain at least 0.1% by weight of an active compound according to the invention but could be varied to be approximately 0.1–50% thereof by weight. The amount of the active ingredient that is contained in such compositions is so high that a suitable dosage is obtained.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic.

For topical administration the compounds according to the invention could be incorporated in a solution, suspension, or ointment. These preparations could contain at least 0.1% by weight of an active compound according to the invention but could be varied to be approximately 0.1–50% thereof by weight. The amount of the active ingredient that is contained in such compositions is so high that a suitable dosage is obtained. The administration could be facilitated by applying touch, pressure, massage, heat, warms, or infrared light on the skin, which leads to enhanced skin permeability. Hirvonen, J., Kalia, Y N, and Guy, R H. Transdermal delivery of peptides by iontophoresis, *Nat Biotechnol* 1996 December; 14(13): 1710–1713 describes how to enhance the transport of a drug via the skin using the driving force of an applied electric field. Preferably, iontophoresis is effected at a slightly basic pH.

Other administration forms are inhalation through the lungs, buccal administration via the mouth, enteral administration via the small intestine, and local administration with a release, preferably a slow release, of the active substance e g in the form of a ring. All these administration forms could be effected by means known by a person skilled in the art.

Another object of the present invention is a compound of the formula (I):

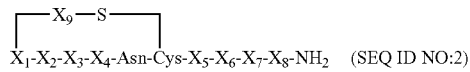

$X_1$-$X_2$-$X_3$-$X_4$-Asn-Cys-$X_5$-$X_6$-$X_7$-$X_8$-NH$_2$   (SEQ ID NO:2)

wherein either:

$X_1$ is Cys, $X_2$ is Tyr, $X_3$ is Ile, $X_4$ is Gln, $X_5$–$X_8$ is nothing, and $X_9$ is S; or $X_1$ is nothing, $X_2$ is Tyr, $X_3$ is Ile, $X_4$ is Gln, $X_5$ is Pro, $X_6$ is Leu, $X_7$ is Gly, $X_8$ is nothing, and $X_9$ is S; or $X_1$–$X_2$ is nothing, $X_3$ is Ile, $X_4$ is Gln, $X_5$ is Pro, $X_6$ is Leu, $X_7$ is Gly, $X_8$ is nothing, and $X_9$ is S; or $X_1$–$X_3$ is nothing, $X_4$ is Gln, $X_5$ is Pro, $X_6$ is Leu, $X_7$ is Leu, $X_8$ is nothing, and $X_9$ is S; or $X_1$–$X_2$ is nothing, $X_3$ is Ile, $X_4$ is Gln, $X_5$ is Pro, $X_6$–$X_8$ is nothing, and $X_9$ is S; as well as salts thereof.

All publications mentioned herein are hereby incorporated by reference. By the expression "comprising" we understand including but not limited to. Thus, other non-mentioned substances, additives or carriers may be present.

The invention will be illuminated by the following Example, which is only intended to illuminate and not restrict the invention in any way.

EXAMPLE 1

Effect of Oxytocin on Cancer in Situ and Cervicitis in Humans

Patients. 20 women, all aged 60–70 years, with postmenopausal disorders, participated in a double blind cross-over randomised protocol, which means that the patients receive both oxytocin and control treatment without knowing the order of the treatments.

Experimental procedure. The patients were treated with oxytocin 1 mg/ml mixed with 1 ml cellulose gel intravaginally during five consecutive days to relieve the postmenopausal disorders. However, it was discovered that one of the patients suffered from cancer in situ and cervicitis before the oxytocin treatment. This was established by the fact that the patient underwent a Pap smear test before the oxytocin treatment. In this test, cells desquamated from the genital epithelium are obtained by smears, fixed and stained, and examined under the microscope for evidence of pathologic changes. After the oxytocin treatment, the patient also underwent a Pap smear test.

Results. When comparing the results of the Pap smear tests before and after oxytocin administration, it was shown that the cancer in situ and cervicitis was removed, implying that oxytocin was efficient for the treatment of cancer in situ and cervicitis.

---

The invention claimed is:

1. A method of treating precancerous conditions in the cervix and vagina, or cancer in the cervix or vagina in a patient in need of treatment thereof, comprising:
   administering to said patient an effective amount of a pharmaceutical composition comprising at least one substance with oxytocin activity,
   wherein said at least one substance with oxytocin activity is of the formula:

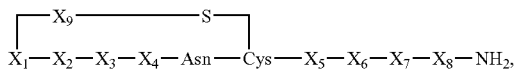

or a salt thereof,
   wherein:
   $X_1$ is Cys, Mpa or nothing;
   $X_2$ is Tyr, (O-Methyl)Tyr, Phe or nothing;
   $X_3$ is Ile, Val, Hoph, Phe, Cha or nothing;
   $X_4$ is Gln, Ser, Thr, Cit, Arg or Daba;
   $X_5$ is Pro or nothing;
   $X_6$ is Ile, Leu, Val, Hos, Daba, Thr, Arg, Cit or nothing;
   $X_7$ is Gly, Ala or nothing;
   $X_8$ is Gly or nothing; and
   $X_9$ is $CH_2$ or S;
   wherein the term "nothing" indicates that the letters $X_1$ $X_2 X_3 X_4 X_5 X_6 X_7$ and $X_8$ respectively have no meaning or represent a bond and that there is a direct bond between the letters, atom, or group situated to the right and to the left, respectiveiy, of the letter designated "nothing".

2. The method according to claim 1, wherein said at least one substance is selected from the group consisting of the following compounds: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

3. The method according to claim 1, wherein said pharmaceutical composition comprises substances that increase the release of oxytocin and/or the number or affinity of oxytocin receptors or drugs having an $\alpha_2$-agonistic effect.

4. The method according to claim 1, wherein said at least one substance is administered in amount of 0.01–100 ng/kg body weight of the patient.

5. The method according to claim 1, wherein said at least one substance is administered in amount of 0.1–10 ng/kg body weight of the patient.

6. The method according to claim 3, wherein said drug having an $\alpha_2$-agonistic effect is clonidine.

7. The method according to claim 3, wherein said substance that increases the release of oxytocin and/or the number or affinity of oxytocin receptors is oestrogen.

8. The method according to claim 2, wherein said pharmaceutical composition comprises substances that increase the release of oxytocin and/or the number or affinity of oxytocin receptors or drugs having an $\alpha_2$-agonistic effect.

9. The method according to claim 8, wherein said drug having an $\alpha_2$-agonistic effect is clonidine.

10. The method according to claim 1, wherein said substance comprises SEQ ID NO: 1.

11. The method according to claim 2, wherein said at least one substance is administered in amount of 0.01–100 ng/kg body weight of the patient.

* * * * *